(12) United States Patent
Sasaki et al.

(10) Patent No.: US 8,971,492 B2
(45) Date of Patent: Mar. 3, 2015

(54) ANALYSIS METHOD FOR X-RAY DIFFRACTION MEASUREMENT DATA

(75) Inventors: Akito Sasaki, Tokyo (JP); Keiichi Morikawa, Tokyo (JP); Akihiro Himeda, Tokyo (JP); Hiroki Yoshida, Tokyo (JP)

(73) Assignee: Rigaku Corporation, Tokyo (JP)

( * ) Notice: Subject to any disclaimer, the term of this patent is extended or adjusted under 35 U.S.C. 154(b) by 294 days.

(21) Appl. No.: 13/600,740

(22) Filed: Aug. 31, 2012

(65) Prior Publication Data

US 2013/0077754 A1 Mar. 28, 2013

(30) Foreign Application Priority Data

Sep. 26, 2011 (JP) .................................. 2011-208339

(51) Int. Cl.
G01N 23/207 (2006.01)
G01N 23/20 (2006.01)
G01J 3/28 (2006.01)

(52) U.S. Cl.
CPC ................ G01N 23/207 (2013.01); G01J 3/28 (2013.01); G01N 23/20 (2013.01)
USPC .................................. 378/71; 378/70; 378/86

(58) Field of Classification Search
USPC ................................................ 378/70, 71, 86
See application file for complete search history.

(56) References Cited

U.S. PATENT DOCUMENTS

| | | | |
|---|---|---|---|
| 5,373,545 A * | 12/1994 | Friedrich et al. ................. | 378/72 |
| 5,414,747 A * | 5/1995 | Ruud et al. ...................... | 378/73 |
| 6,269,144 B1 * | 7/2001 | Dube et al. ...................... | 378/71 |
| 6,385,289 B1 * | 5/2002 | Kikuchi .......................... | 378/79 |
| 6,678,347 B1 * | 1/2004 | Kozaczek et al. ................ | 378/75 |
| 6,697,454 B1 * | 2/2004 | Nicolich et al. ................. | 378/85 |
| 6,751,287 B1 * | 6/2004 | Kalyon et al. .................. | 378/71 |
| 6,882,739 B2 * | 4/2005 | Kurtz et al. ................... | 382/109 |

(Continued)

FOREIGN PATENT DOCUMENTS

| | | |
|---|---|---|
| JP | 4-29046 A | 1/1992 |
| JP | 7-083857 A | 3/1995 |
| JP | 8-043327 A | 2/1996 |
| JP | 11-064251 A | 3/1999 |
| JP | 11-84015 A | 3/1999 |
| JP | 2001-152374 A | 6/2001 |
| JP | 4658003 B2 | 3/2011 |

OTHER PUBLICATIONS

Japanese Office Action dated Apr. 2, 2014, issued in Japanese Patent Application No. 2011-208339, w/English translation (6 pages).

*Primary Examiner* — David A Vanore
(74) *Attorney, Agent, or Firm* — Westerman, Hattori, Daniels & Adrian, LLP

(57) ABSTRACT

Peak positions and integrated intensities of diffraction X-ray are determined on the basis of X-ray diffraction measurement data output from an X-ray diffractometer, the number of determined peaks of the diffraction X-ray is counted, and analysis processing is started when the counted number of peaks reaches a preset peak number. The analysis processing is repetitively executed on the basis of X-ray diffraction measurement data. The peak positions and the integrated intensities of the diffraction X-ray are determined from the X-ray diffraction measurement data obtained from the start of the measurement till the analysis processing concerned, and qualitative analysis of collating the determined peak positions and integrated intensities with standard peak card data whose data base is made in advance and searching materials contained in a measurement sample, and quantitative analysis of determining the quantities of the materials contained in the measurement sample are executed.

7 Claims, 11 Drawing Sheets

(56) References Cited

U.S. PATENT DOCUMENTS

| | | |
|---|---|---|
| 7,039,158 B1 * | 5/2006 | Janik et al. .................... 378/45 |
| 7,039,161 B2 * | 5/2006 | Ito et al. ........................ 378/86 |
| 7,158,609 B2 * | 1/2007 | Kikuchi et al. ................ 378/73 |
| 7,206,378 B2 * | 4/2007 | Obata et al. ................... 378/71 |
| 7,508,907 B2 * | 3/2009 | Sasayama ...................... 378/45 |
| 7,519,153 B1 * | 4/2009 | Moore ........................... 378/70 |
| 8,155,267 B2 * | 4/2012 | Hodeau et al. ................. 378/44 |
| 2003/0012334 A1 * | 1/2003 | Kurtz et al. ................... 378/73 |
| 2005/0190881 A1 * | 9/2005 | Obata et al. ................... 378/87 |

* cited by examiner

ANALYSIS METHOD FOR X-RAY DIFFRACTION MEASUREMENT DATA

FIELD OF THE INVENTION

The present invention relates to a method of analyzing measurement data obtained by an X-ray diffractometer.

BACKGROUND OF THE INVENTION

It is well known that materials contained in a measurement sample can be identified (qualitative analysis) and the quantities of the materials can be analyzed (quantitative analysis) according to an X-ray diffraction measurement. According to a conventional X-ray diffraction measurement, X-ray diffraction measurement using an X-ray diffractometer is executed on a sample, and all measurement data are processed to perform qualitative analysis or quantitative analysis after the measurement is finished (see Patent Document 1 or Patent Document 2, for example).

The X-ray diffraction measurement and the data analysis thereof are used in, for example, an inspection process for inspecting whether target chemical materials are manufactured in a synthesizing plant of chemical materials. In this type of synthesizing plant, incase that manufactured chemical materials are greatly different from target chemical materials, it is required to immediately stop the operation and quest for a cause. Therefore, there has been desired a method of rapidly performing not only high-precision analysis of manufactured chemical materials, but also simple screening in the inspection process so as to discriminate products which are clearly different from the target chemical materials.

PRIOR ART DOCUMENT 1

[Patent Document 1] JP-A-11-64251
[Patent Document 2] JP-A-7-83857

SUMMARY OF THE INVENTION

The present invention has been implemented in view of the foregoing circumstances, and has an object to provide an analysis method for X-ray diffraction measurement data obtained by rapidly performing simple screening.

In order to attain the above object, the present invention is characterized in that analysis of X-ray diffraction measurement data output from an X-ray diffractometer is repetitively executed in parallel to X-ray diffraction measurement based on the X-ray diffractometer.

According to the present invention, the analysis of the X-ray diffraction measurement data is repetitively executed in parallel to the X-ray diffraction measurement based on the X-ray diffractometer, so that an analysis result in the middle of analysis processing can be obtained without waiting for the end of the X-ray diffraction measurement. Accordingly, simple screening can be rapidly performed by using the analysis result concerned.

Here, it is preferable in this method that peak positions and integrated intensities of diffraction X-ray are determined on the basis of the X-ray diffraction measurement data output from the X-ray diffractometer, the number of determined peaks of the diffraction X-ray is counted and the analysis of the X-ray diffraction measurement data is started when the counted peak number reaches a preset peak number.

In most cases, no peak appears in diffraction X-ray as an analysis target for a short while from start of the X-ray diffraction measurement based on the X-ray diffractometer. The analysis of the X-ray diffraction measurement data is not executed for this time period, thereby reducing a load imposed on equipment such as a computer or the like used for data analysis.

It is preferable in this method that after the analysis of the X-ray diffraction measurement data is started, next analysis may be executed on the basis of X-ray diffraction measurement data which have been obtained from the start of the measurement until the analysis processing is finished every the analysis processing is finished.

By repeating the analysis processing as described above, the analysis precision is gradually enhanced.

Furthermore, the analysis of the X-ray diffraction measurement data may contain qualitative analysis of collating the peak positions and the integrated intensities of the diffraction X-ray determined from the X-ray diffraction measurement data obtained from the start of the measurement till the analysis processing with standard peak card data whose data base is made in advance to search materials contained in a measurement sample.

As described above, the qualitative analysis is executed on the basis of the X-ray diffraction measurement data which have been obtained from the start of the measurement till then, whereby materials contained in the measurement sample can be roughly determined although the precision is still low.

Furthermore, it is preferable that the analysis of the X-ray diffraction measurement data contains not only the qualitative analysis, but also quantitative analysis of determining the quantities of the materials contained in the measurement sample on the basis of the X-ray diffraction measurement data obtained from the start of the measurement till the analysis processing.

The quantities of the materials contained in the measurement sample can be determined on the basis of the analysis result although the precision of the quantitative analysis is still low.

As described above, the qualitative analysis and the quantitative analysis which are performed in parallel to the X-ray diffraction measurement are still low in precision. Therefore, it is uncertain to determine materials contained in the measurement sample on the basis of the analysis result.

Therefore, it is preferable in this method that qualitative analysis of collating peak positions and integrated intensities of diffraction X-ray determined from all X-ray diffraction measurement data obtained from the start of the measurement till the end of the measurement and output from the X-ray diffractometer with standard peak card data whose data base is made in advance to search the materials contained in the measurement sample is executed after the X-ray diffraction measurement based on the X-ray diffractometer is finished.

Furthermore, it is preferable in this method that quantitative analysis of determining the quantities of the materials contained in the measurement sample on the basis of all the X-ray diffraction measurement data obtained from the start of the measurement till the end of the measurement and output from the X-ray diffractometer is executed after the X-ray diffraction measurement based on the X-ray diffractometer is finished.

As described above, according to the present invention, the analysis of the X-ray diffraction measurement data output from the X-ray diffractometer is repetitively executed in parallel to the X-ray diffraction measurement based on the X-ray diffractometer. Therefore, an analysis result in the middle of the analysis processing can be obtained without waiting for the end of the X-ray diffraction measurement, and simple screening can be rapidly performed by using the analysis result.

DETAILED DESCRIPTION OF EMBODIMENTS

Embodiments according to the present invention will be described in detail with reference to the drawings.

Figure 1:
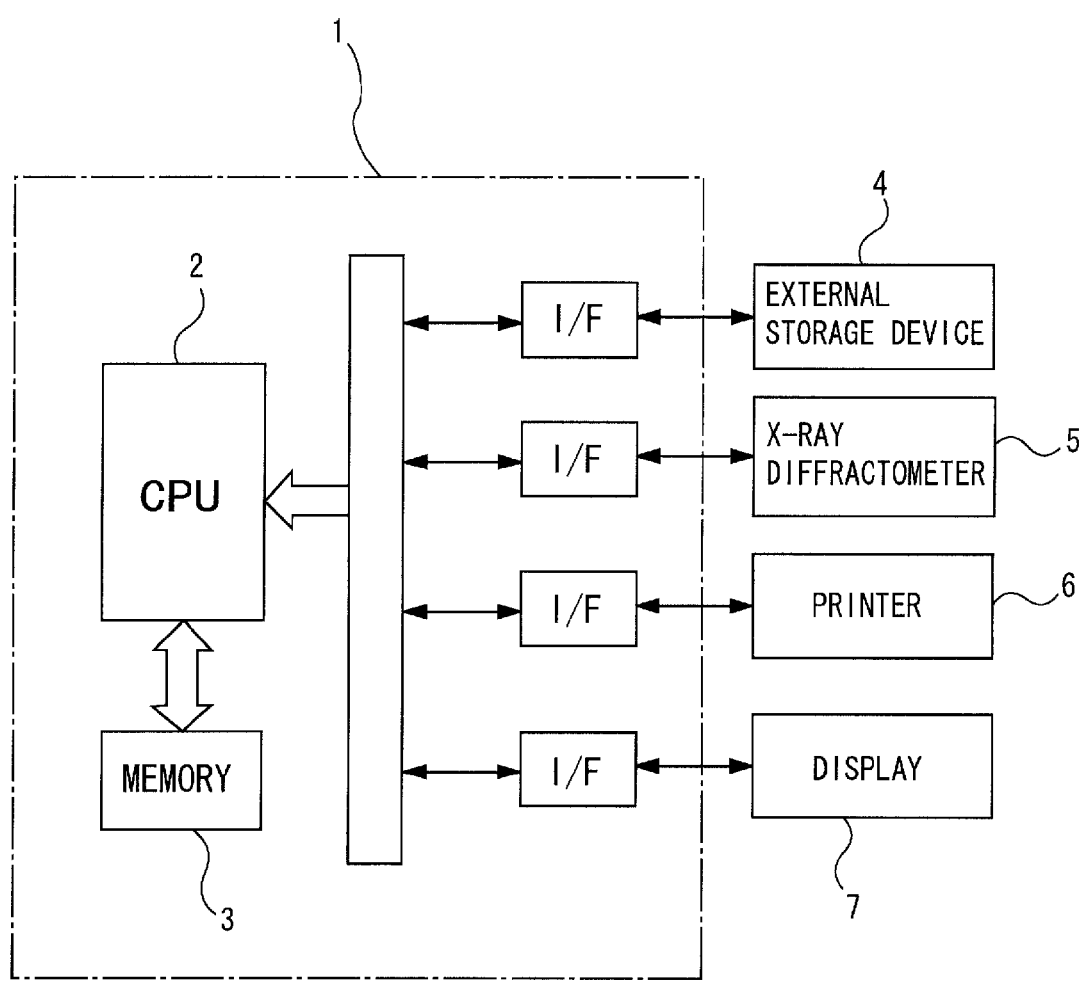
FIG. 1 is a block diagram showing an example of the construction of an analysis system used to execute an analysis method for X-ray diffraction measurement data according to the present invention.

FIG. 1 is a block diagram showing an example of the construction of an analysis system used to execute an analysis method for X-ray diffraction measurement data according to the present invention.

This analysis system has a computer 1 for executing overall control of analysis processing, and the computer 1 has CPU (Central Processing Unit) 2, a semiconductor memory 3 for storing various kinds of data so that the data can be read and written, and interfaces I/F each of which is disposed between the computer and each of various kinds of external equipment.

For example, an external storage device 4 such as a hard disk or the like, an X-ray diffractometer 5 as measurement equipment, and a printer 6 and a display 7 as output equipment are connected to the respective interfaces I/F.

Programs for executing the analysis processing and a standard peak card data base to be referred to for search of materials contained in measurement samples are stored in the external storage device 4 in advance, and also various kinds of data such as measurement data output from the X-ray diffractometer 5, analysis data obtained by executing the analysis processing in CPU 2, etc. are further stored in the external storage device 4.

The standard peak card is widely known as, for example, ICDD (International Centre for Diffraction Data) file or the like, and peak search results based on standard X-ray diffraction profiles obtained when X-ray diffraction measurement is performed on any kinds of chemical compounds by using a standard X-ray optical system in advance are collected in the form of a card every kind of chemical compound. The content of the card is stored in the form of table data in the external storage device 4.

Figure 2:
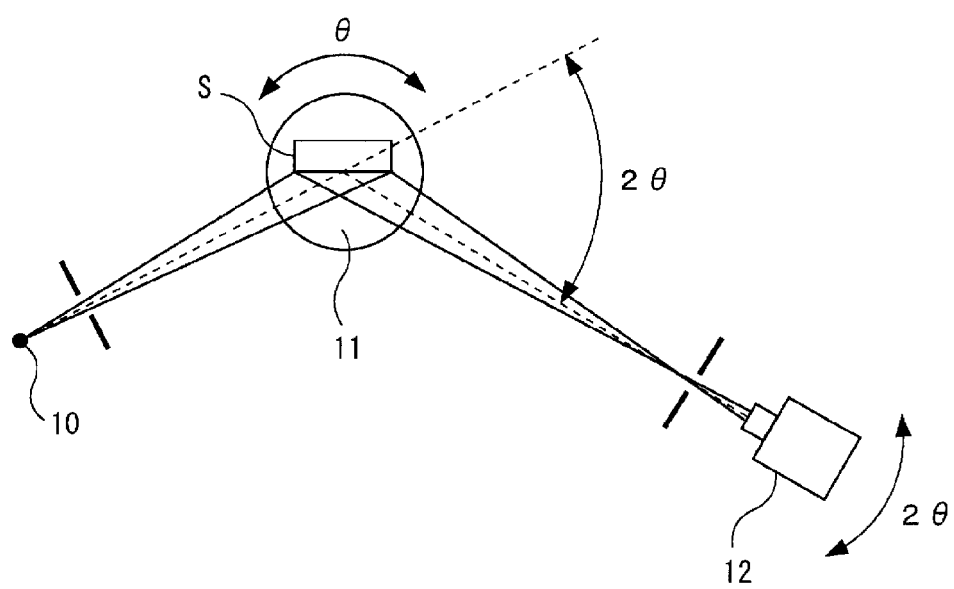
FIG. 2 is a diagram showing an example of the construction of an X-ray diffractometer.

For example, as shown in FIG. 2, the X-ray diffractometer 5 has an X-ray source 10, a sample rotating system 11 for rotating a measurement sample S stepwise or continuously at a suitable angular velocity, that is, subjecting the measurement sample S to $\theta$-rotation, and an X-ray detector 12 which rotates around the measurement sample S in the same direction at an angular velocity which is twice as high as the $\theta$-rotation, that is, is subjected to $2\theta$ rotation. Since the structure and function of the X-ray diffractometer 5 have been already known, the detailed description thereof is omitted.

Next, a method of analyzing X-ray diffraction measurement data by using the X-ray diffractometer 5 described above and an analysis system will be described.

Figure 3:
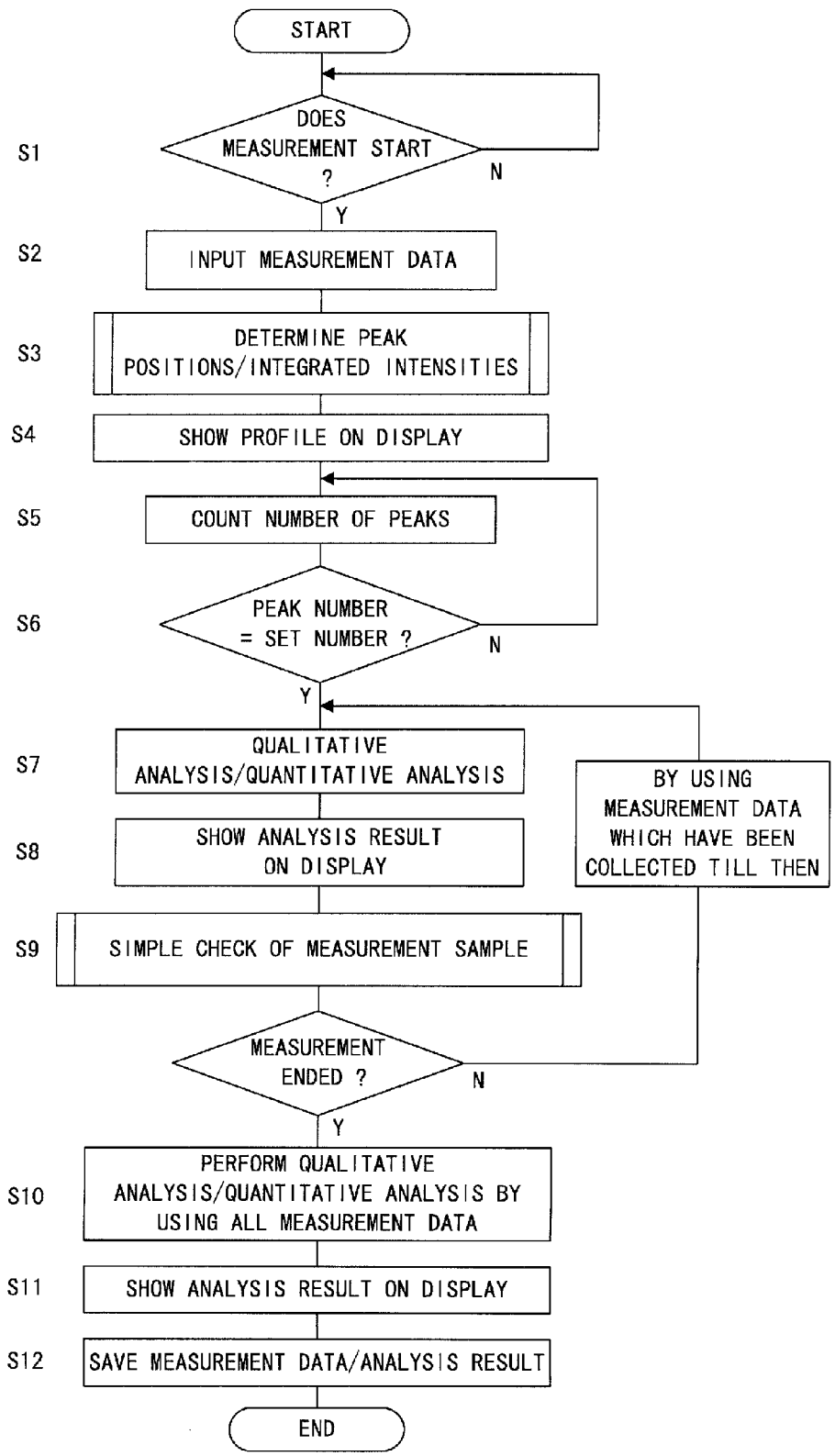
FIG. 3 is a flowchart showing the analysis method for X-ray diffraction measurement data according to the embodiment of the present invention.
Figure 4:
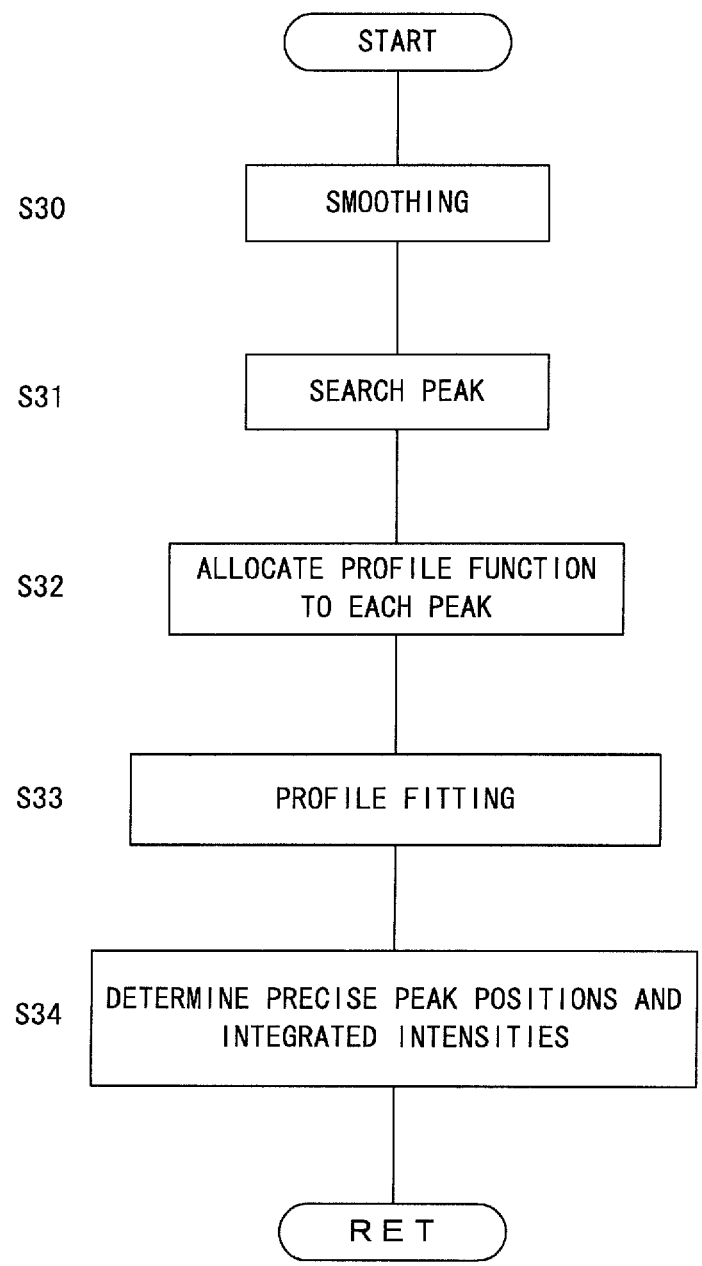
FIG. 4 is a flowchart showing the flow of analysis processing of peak positions and integrated intensities.
Figure 5:
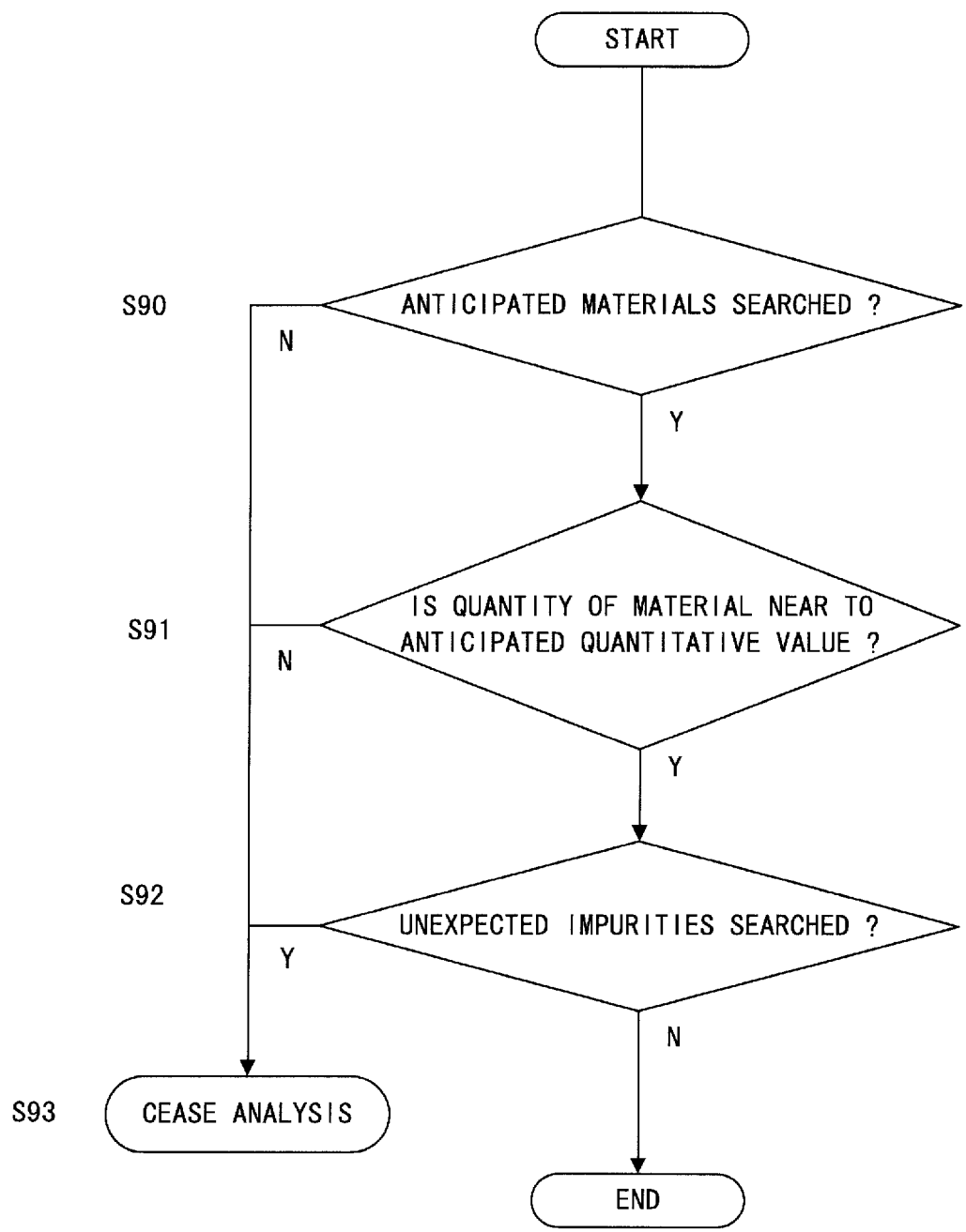
FIG. 5 is a flowchart showing the processing procedure of simple determination for a measurement sample.
Figure 6:
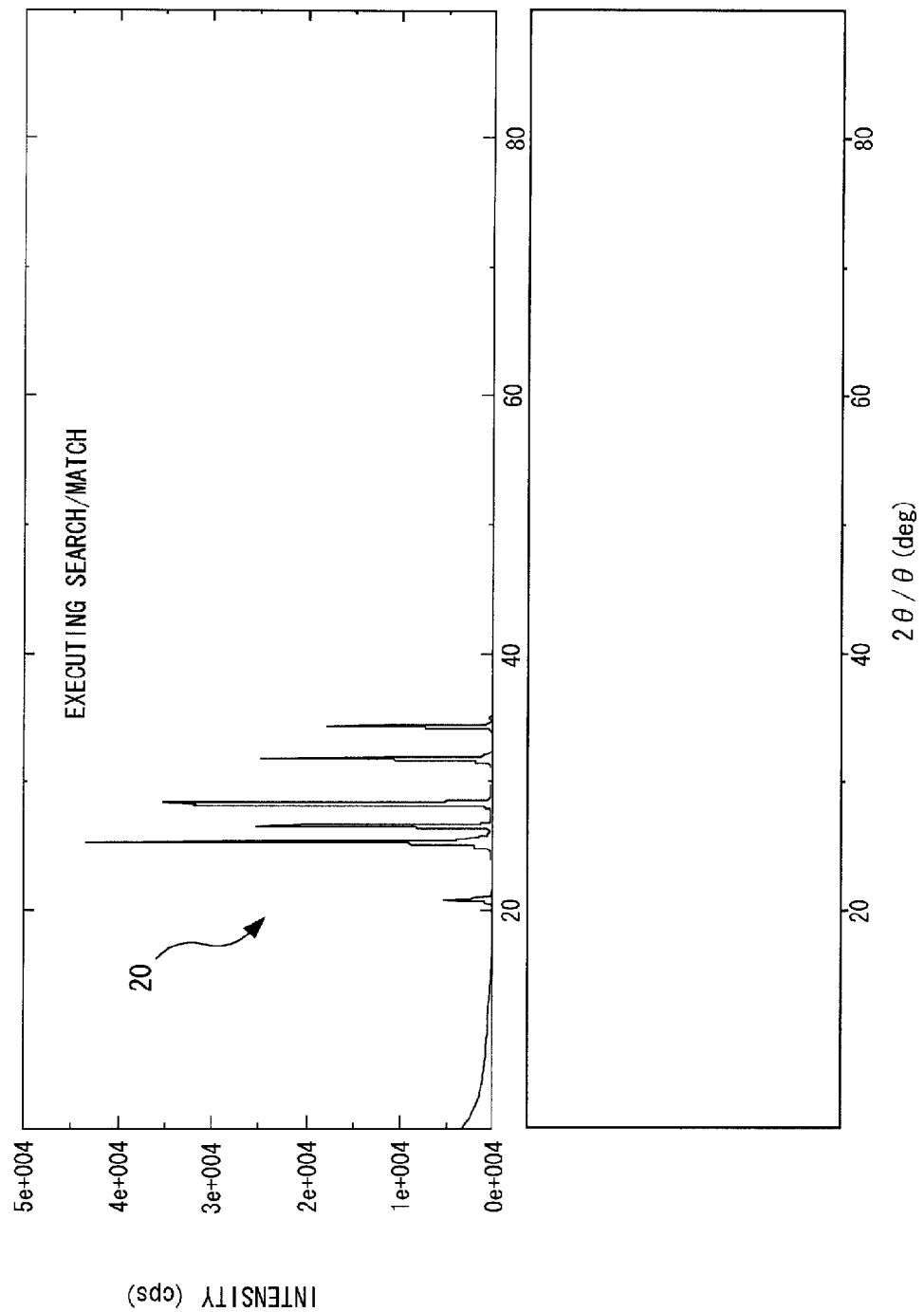
FIG. 6 is a diagram showing an example of an image shown on a display in connection with the progression of the analysis processing of measurement data.

FIGS. 3 to 5 are flowcharts showing the analysis method of the X-ray diffraction measurement data according to this embodiment.

As shown in FIG. 3, when the X-ray diffractometer 5 starts X-ray diffraction measurement for the measurement sample S (step S1), an analysis system inputs X-ray diffraction measurement data (hereinafter referred to as measurement data) from the X-ray diffractometer 5 (step S2), and successively determines peak positions and integrated intensities (step S3). When the measurement data are two-dimensional data, the two-dimensional data are transformed to one-dimensional data before analysis processing.

FIG. 4 shows the flow of the analysis processing of the peak positions and the integrated intensities. The analysis of the peak positions and the integrated intensities shown in FIG. 3 (step S3) is processed according to the procedure shown in FIG. 4. That is, CPU 2 of the analysis system first smoothens the input measurement data (step S30). Subsequently, peaks of the smoothened measurement data are searched by using a publicly known analysis method such as a quadratic differential method or the like (step S31). A publicly known function such as a divisional type pseudo Voigt function or the like is allocated to each of the thus-specified peaks of the measured data as a profile function (step S32). Furthermore, profile fitting is executed on each peak of the measurement data by using a publicly known analysis method such as a least-square method or the like (step S33). The peak positions and the integrated intensities are precisely determined from the values of the respective parameters of the thus-obtained profile function (step S34).

Returning to FIG. 3, the X-ray diffraction profile 20 obtained through the analysis processing of the peak positions and the integrated intensities is shown in an image on the display 7 (step S4). FIGS. 6 to 11 show images shown on the display 7 in connection with the progression of the analysis processing of the measurement data. As shown in these figures, the X-ray diffraction profile 20 is drawn on a graph plotting the X-ray intensity on the ordinate axis and the diffraction angle $2\theta$ on the abscissa axis.

The respective processing of the analysis of the peak positions/integrated intensities (step S3) from the input of the measurement data (step S2) and the display of the X-ray diffraction profile 20 onto the display 7 (step S4) are continuously performed in conformity with the progression of the X-ray diffraction measurement. Accordingly, the X-ray diffraction profile 20 shown on the display 7 successively extends from a low angle side (the left side of the figures) of the diffraction angle 2θ to a high angle side (the right side of the figures) of the diffraction angle 2θ.

Subsequently, the number of the peak positions obtained in step S3 is counted (step s5), and when the number of the peak positions reaches a preset peak number (step S6), simple qualitative analysis and quantitative analysis are started on the basis of the peak positions and the integrated intensities analyzed from the measurement data which have been obtained till then (step S7). Any number may be set as the number of peaks as a trigger for starting the simple qualitative analysis and quantitative analysis. For example, when the set number is set to five, the simple qualitative analysis and quantitative analysis are started when five peak positions are counted from the start of the measurement.

In this case, the qualitative analysis and the quantitative analysis may be performed by using publicly known analysis methods.

For example, the qualitative analysis may be performed by the method using the standard peak card data described above. That is, peak positions and integrated intensities of diffraction X-ray which have been obtained in step S3 from the start of the measurement until the execution of the qualitative analysis (that is, until the set number of peaks are counted) are collated with standard peak card data whose data base is made in advance, and materials contained in the measurement sample S are searched.

Furthermore, the quantitative analysis may be performed by using the analysis method disclosed in JP-A-2009-168584 previously proposed by this applicant, for example. That is, the integration amount of peak waveforms contained in the X-ray diffraction profile 20 is determined, and the content of materials contained in the measurement sample S is determined from the integration amount on the basis of a standard curve.

The peak positions coincident with the searched materials, the standard peak card data of the materials concerned and the quantitative rates of the searched materials are shown as an analysis result on the display 7 (step S8) every time the analysis processing of the step S7 is finished. A display represented by reference numeral 21 in FIGS. 7 to 11 is standard peak card data, and displays represented by reference numeral 22 are quantitative rates of the searched materials. Furthermore, the peak positions coincident with the search materials are shown with being superimposed on the image of the X-ray diffraction profile 20.

Next, in this embodiment, a processing step of automatically performing simple check of the measurement sample S on the basis of the analysis result obtained in step S7 is provided (step S9).

FIG. 5 shows the processing procedure of the simple check of the measurement sample S. As shown in FIG. 5, in the processing step of the simple check, the materials searched in step S7 are collated with materials which are pre-estimated as materials contained in the measurement sample S (step S90). Furthermore, the measurement sample S is subjected to the simple check by using, as a criterion for check, whether the materials searched in step S7 are unexpected impurities (that is, materials which are impossible to be contained).

The materials contained in the measurement sample S and the impurities which are impossible to be contained in the measurement sample S can be anticipated from the manufacturing process of the measurement sample S mounted in the X-ray diffractometer 5. Therefore, they are stored in the external storage device 4 in advance.

When the determination result indicates that no anticipated material is searched, the quantity of a searched material is greatly deviated from an anticipated quantitative value or unexpected impurities are searched, a critical problem may occur in the manufacturing process of the measurement sample S. Therefore, when such a determination result is obtained, the analysis is ceased and the determination result is informed (step S93).

Returning to FIG. 3, the processing from the step S7 to the step S9 is repetitively executed by using the measurement data which have been collected until the X-ray diffraction measurement is finished. That is, after analysis of X-ray diffraction measurement data is started, the next analysis (the qualitative analysis and the quantitative analysis) is executed and repeated on the basis of the X-ray diffraction measurement data which have been obtained from the start of the measurement until the analysis processing is finished every time the analysis processing is finished.

The analysis result obtained in step S7 is low in precision because it is obtained by the simple processing executed on the basis of a small amount of measurement data. Accordingly, the analysis result obtained in step S7 normally varies as the analysis processing progresses.

Figure 7:
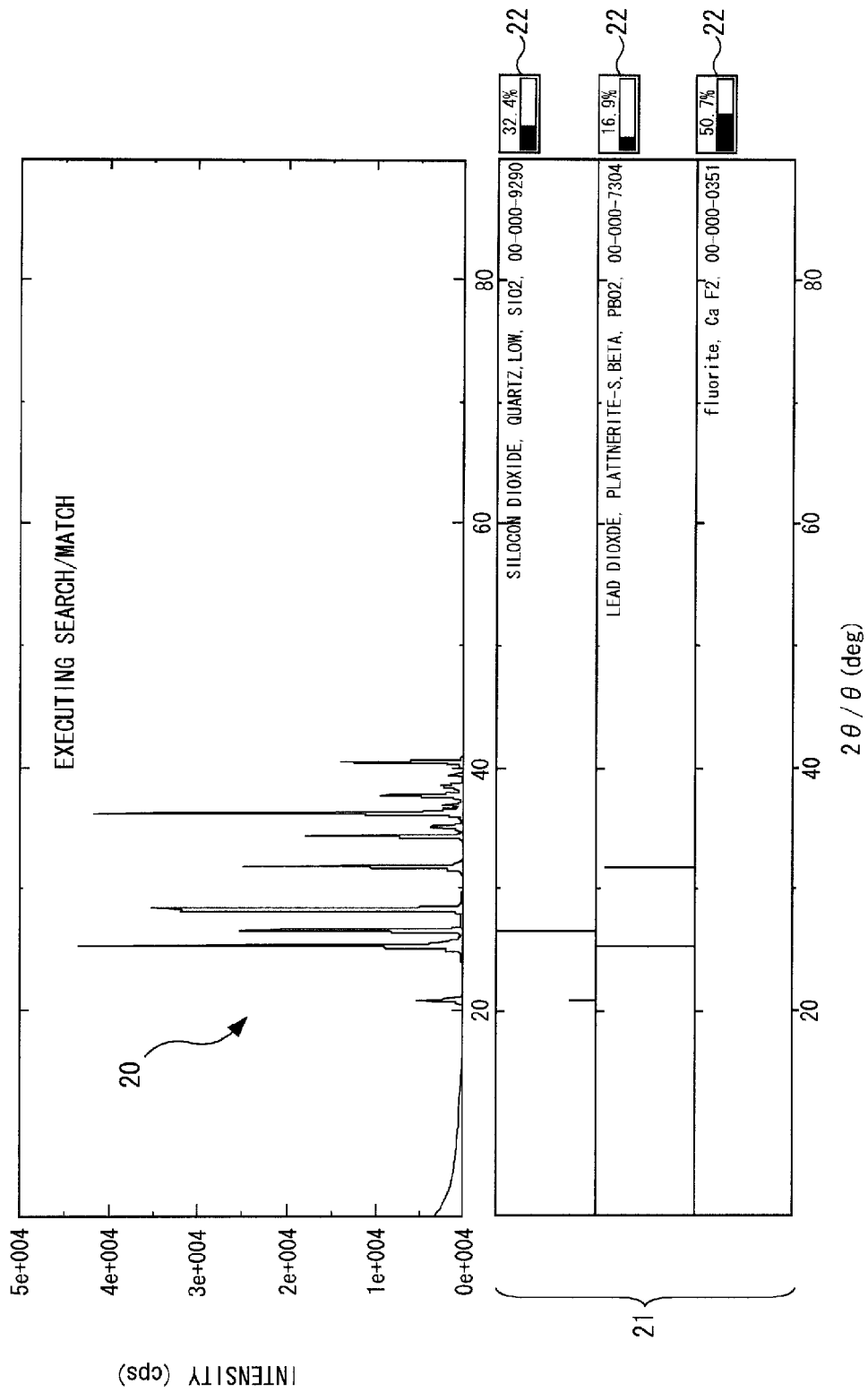
FIG. 7 is a diagram which is subsequent to FIG. 6 and shows an example of an image shown on the display in connection with the progression of the analysis processing of measurement data.
Figure 8:
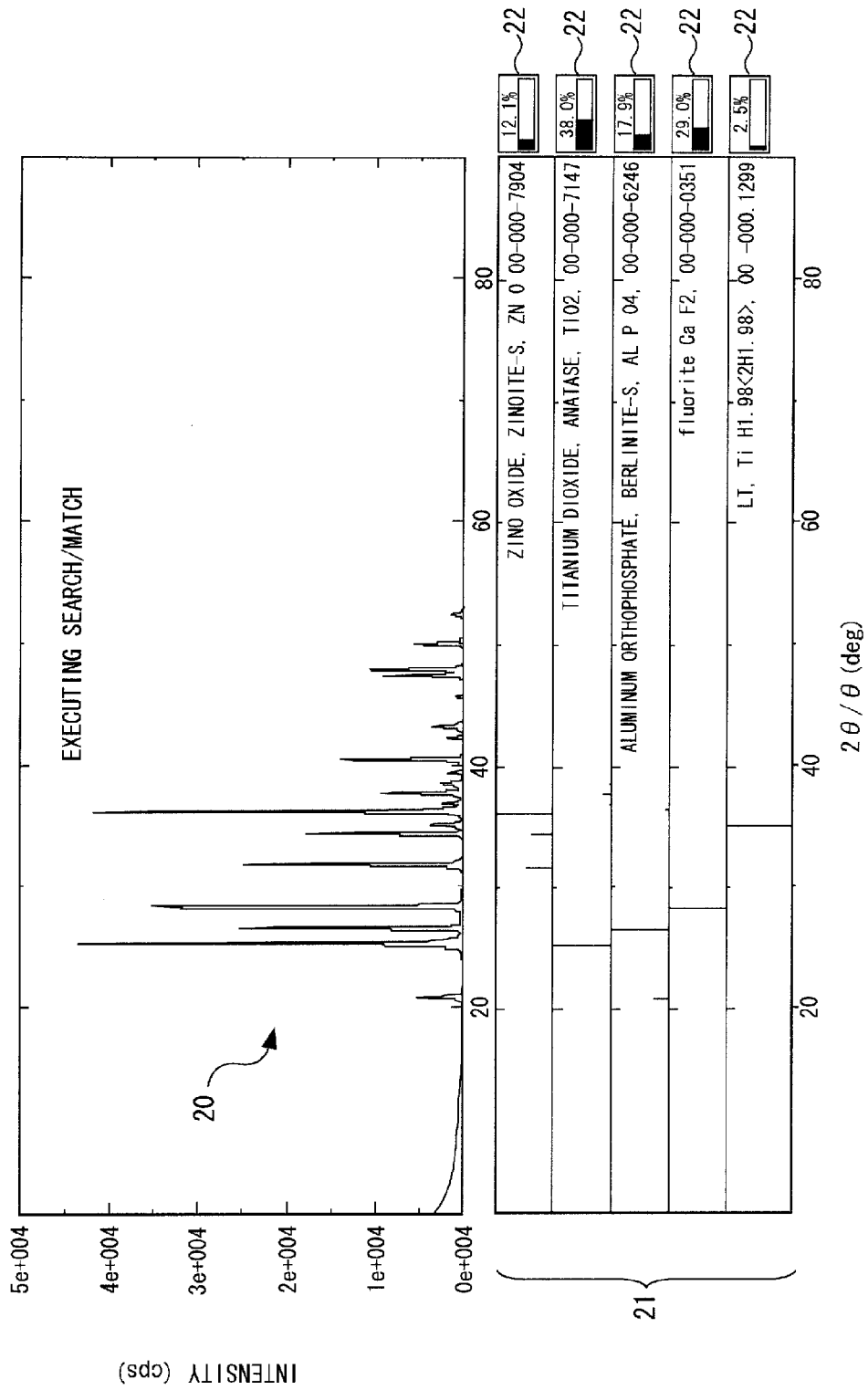
FIG. 8 is a diagram which is subsequent to FIG. 7 and shows an example of an image shown on the display in connection with the progression of the analysis processing of measurement data.
Figure 9:
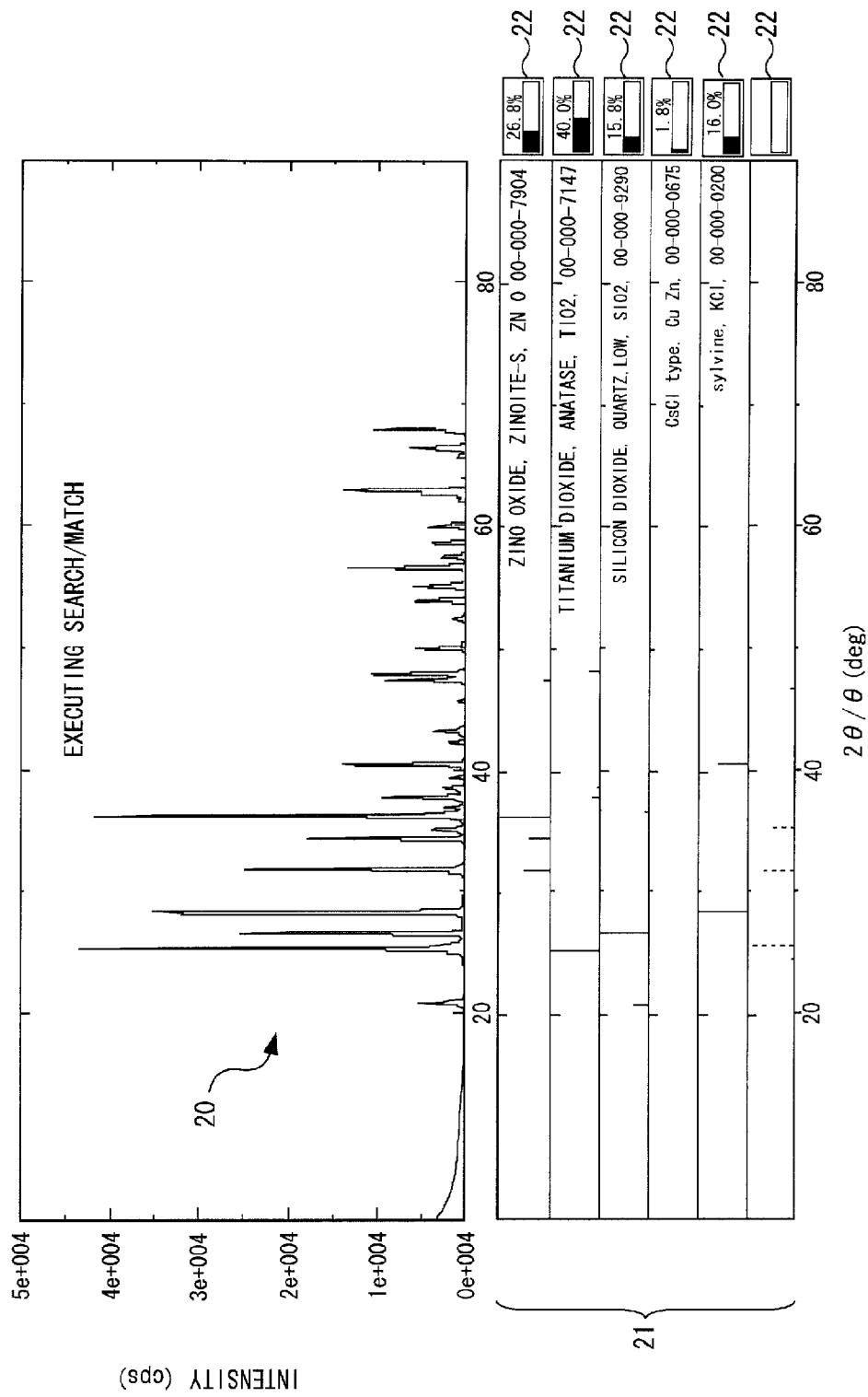
FIG. 9 is a diagram which is subsequent to FIG. 8 and shows an example of an image shown on the display in connection with the progression of the analysis processing of measurement data.
Figure 10:
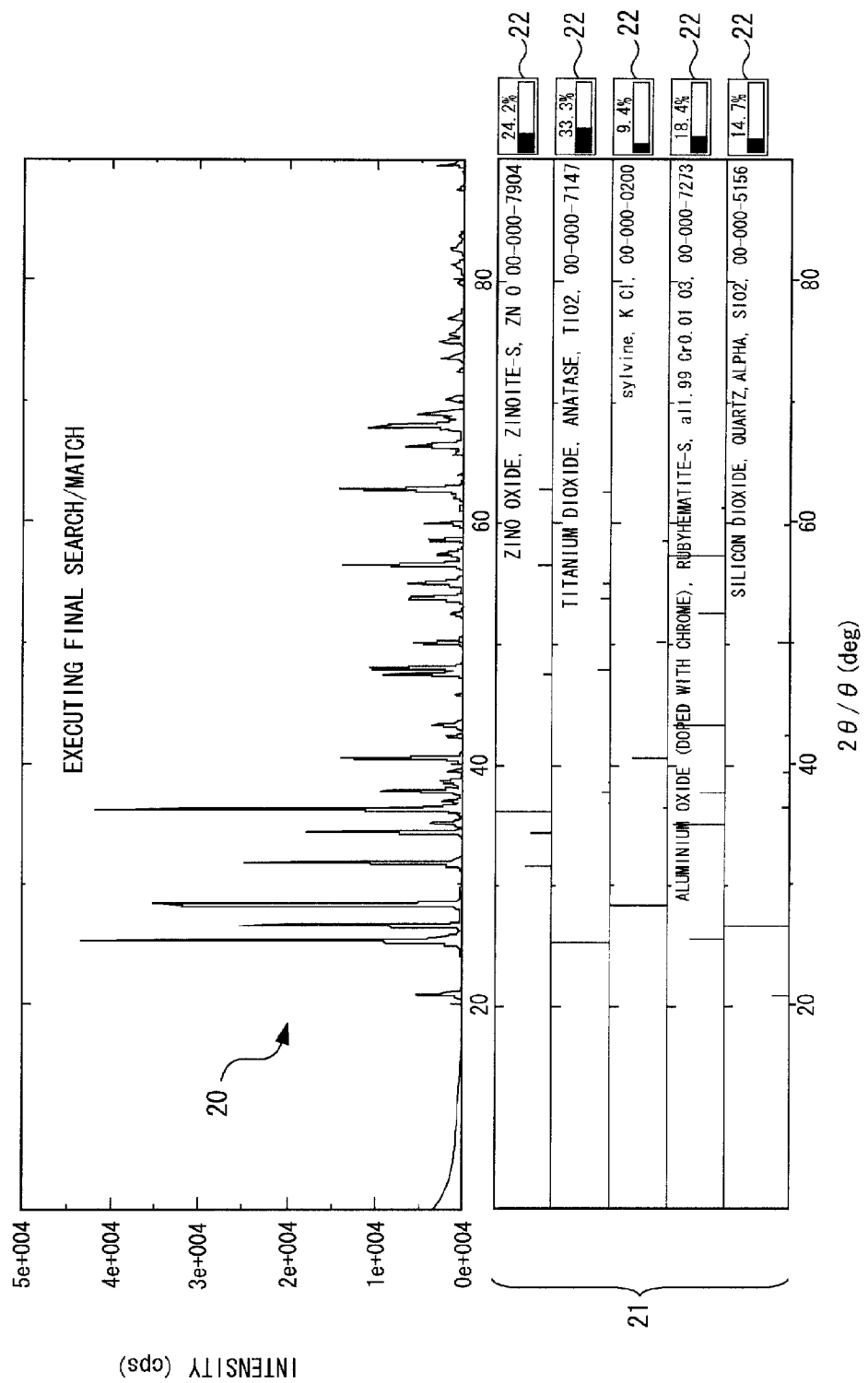
FIG. 10 is a diagram which is subsequent to FIG. 9 and shows an example of an image shown on the display in connection with the progression of the analysis processing of measurement data.

For example, referring to FIGS. 7 to 10, it is apparent that the types of the standard peak card data 21 of the searched materials and the quantitative rates 22 of the materials are successively changed in conformity with the progression of the measurement as the measurement progresses from FIG. 7 showing the analysis result at the initial stage through FIGS. 8 and 9 to FIG. 10.

It is needless to say that the precision of the analysis result increases as the measurement progresses because the amount of the measurement data for the analysis processing increases.

When the X-ray diffraction measurement is finished, the peak positions and the integrated intensities are re-determined by using all the finally obtained measurement data, the qualitative analysis is executed, and also the precise quantitative analysis is executed on the basis of the whole pattern fitting (WPPF) (step S10).

The measurement sample S can be finally identified with high precision by using the thus-obtained analysis result.

Figure 11:
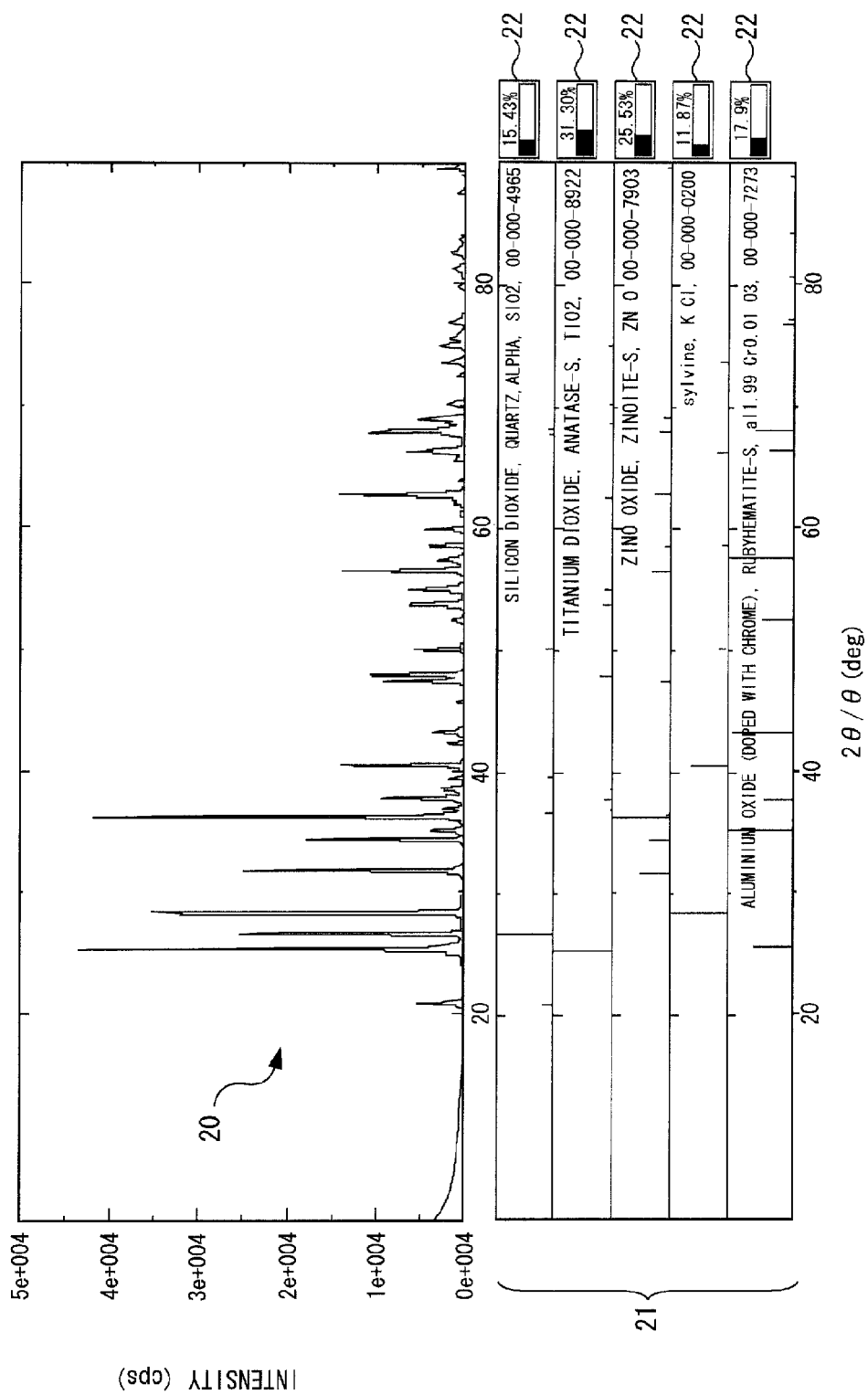
FIG. 11 is a diagram showing an example of an image obtained by showing a final analysis processing result of measurement data on the display.

As shown in FIG. 11, the final analysis result obtained in step S10 is shown on the display 7 (step S11). The measurement data and the analysis result are saved in the external storage device 4, and all the steps of the analysis processing are finished (step S12).

It is needless to say that the present invention is not limited to the above embodiment and various modifications and applications may be made.

For example, the analysis processing after the analysis of the X-ray diffraction measurement data is started may be executed at the following timing.

(a) The next analysis is executed every preset measurement angle on the basis of X-ray diffraction measurement which have been obtained from the start of the measurement till the measurement angle concerned.

(b) The next analysis is executed every preset time interval on the basis of X-ray diffraction measurement which have been obtained from the start of the measurement till the time interval concerned.

(c) Peak positions and integrated intensities of diffraction X-ray are determined on the basis of X-ray diffraction measurement data output from the X-ray diffractometer, the number of determined peaks of the diffraction X-ray is counted and the next analysis is executed every time the counted peak number reaches a preset peak number.

(d) A peak position and an integrated intensity of diffraction X-ray are determined on the basis of X-ray diffraction measurement data output from the X-ray diffractometer, and the next analysis is executed every time a diffraction X-ray peak appears.

When analysis processing is executed at any one of these timings (a) to (d), it is conditioned that whether the just-before analysis processing is finished before the above analysis processing is executed is determined and the just-before analysis processing has been finished.

The invention claimed is:

1. An analysis method for X-ray diffraction measurement data, comprising the steps of:
    repetitively executing analysis of X-ray diffraction measurement data output from an X-ray diffractometer on the basis of the X-ray diffraction measurement data in parallel to X-ray diffraction measurement based on the X-ray diffractometer;
    determining peak positions and integrated intensities of diffraction peaks on the basis of the X-ray diffraction measurement data output from the X-ray diffractometer; and
    counting the number of determined diffraction peaks is counted, the analysis of the X-ray diffraction measurement data being started when the counted peak number reaches a preset peak number.

2. The analysis method for X-ray diffraction measurement data according to claim 1, wherein after the analysis of the X-ray diffraction measurement data is started, next analysis is executed on the basis of X-ray diffraction measurement data which have been obtained from the start of the measurement until the analysis processing is finished.

3. The analysis method for X-ray diffraction measurement data according to claim 2, wherein the analysis of the X-ray diffraction measurement data contains qualitative analysis of collating the peak positions and the integrated intensities of the diffraction peaks determined from the X-ray diffraction measurement data obtained from the start of the measurement till the analysis processing with standard peak card data whose data base is made in advance to search materials contained in a measurement sample.

4. The analysis method for X-ray diffraction measurement data according to claim 3, wherein the analysis of the X-ray diffraction measurement data contains not only the qualitative analysis, but also quantitative analysis of determining the quantities of the materials contained in the measurement sample on the basis of the X-ray diffraction measurement data obtained from the start of the measurement till the analysis processing.

5. The analysis method for X-ray diffraction measurement data according to claim 4, wherein qualitative analysis of collating peak positions and integrated intensities of diffraction peaks determined from all X-ray diffraction measurement data obtained from the start of the measurement till the end of the measurement and output from the X-ray diffractometer with standard peak card data whose data base is made in advance to search the materials contained in the measurement sample is executed after the X-ray diffraction measurement based on the X-ray diffractometer is finished.

6. The analysis method for X-ray diffraction measurement data according to claim 5, wherein quantitative analysis of determining the quantities of the materials contained in the measurement sample on the basis of all the X-ray diffraction measurement data obtained from the start of the measurement till the end of the measurement and output from the X-ray diffractometer is executed after the X-ray diffraction measurement based on the X-ray diffractometer is finished.

7. An analysis method for X-ray diffraction measurement data, comprising the steps of:
    repetitively executing analysis of X-ray diffraction measurement data output from an X-ray diffractometer on the basis of the X-ray diffraction measurement data in parallel to X-ray diffraction measurement based on the X-ray diffractometer;
    determining peak positions and integrated intensities of diffraction peaks on the basis of the X-ray diffraction measurement data output from the X-ray diffractometer;
    counting the number of determined peaks of the diffraction X-ray, the analysis of the X-ray diffraction measurement data being started when the counted peak number reaches a preset peak number; and
    executing a next analysis on the basis of X-ray diffraction measurement data which have been obtained from the start of the measurement until the analysis processing is finished, wherein
    the analysis of the X-ray diffraction measurement data contains qualitative analysis of collating the peak positions and the integrated intensities of the diffraction peaks determined from the X-ray diffraction measurement data obtained from the start of the measurement till the analysis processing with standard peak card data whose data base is made in advance to search materials contained in a measurement sample,
    the analysis of the X-ray diffraction measurement data contains not only the qualitative analysis, but also quantitative analysis of determining the quantities of the materials contained in the measurement sample on the basis of the X-ray diffraction measurement data obtained from the start of the measurement till the analysis processing,
    qualitative analysis of collating peak positions and integrated intensities of diffraction peaks determined from all X-ray diffraction measurement data obtained from the start of the measurement till the end of the measurement and output from the X-ray diffractometer with standard peak card data whose data base is made in advance to search the materials contained in the measurement sample is executed after the X-ray diffraction measurement based on the X-ray diffractometer is finished, and
    quantitative analysis of determining the quantities of the materials contained in the measurement sample on the basis of all the X-ray diffraction measurement data obtained from the start of the measurement till the end of the measurement and output from the X-ray diffractometer is executed after the X-ray diffraction measurement based on the X-ray diffractometer is finished.

* * * * *